United States Patent
Barmada

Patent Number: 5,443,501
Date of Patent: Aug. 22, 1995

[54] METHOD FOR MAKING AN ARTIFICIAL HEART VALVE

[76] Inventor: Hazem Barmada, 1132 Cedar St., Lake Oswego, Oreg. 97034

[21] Appl. No.: 97,763

[22] Filed: Jul. 26, 1993

[51] Int. Cl.⁶ ............................................. A61F 2/24
[52] U.S. Cl. ...................................... 623/2; 623/901; 356/357
[58] Field of Search ................... 623/2, 901; 356/357, 356/358; 250/563

[56] References Cited

U.S. PATENT DOCUMENTS

| | | | |
|---|---|---|---|
| 4,078,268 | 3/1978 | Possis. | |
| 4,276,658 | 7/1981 | Hanson et al. | |
| 5,116,369 | 5/1992 | Kushibiki et al. | 623/6 |
| 5,133,601 | 7/1992 | Cohen et al. | 356/359 |

FOREIGN PATENT DOCUMENTS

| | | | |
|---|---|---|---|
| 1538047 | 1/1990 | U.S.S.R. | 356/359 |
| 9008518 | 8/1990 | WIPO | 623/2 |

OTHER PUBLICATIONS

Burckhardt et al., "Heart Valve Replacement with St. Jude Medical Valve Prosthesis," *Supplement I Circulation* 78:18–24 (1988).

Caber, "An Interferometric Profiler for Rough Surfaces," five-page paper printed by WYKO Corporation (Jan. 1992).

Koja et al., "Five-year Clinical Evaluation [sic] of the St. Jude Medical Valve Prosthesis in 136 Patients," *Jap. J. Surg.* 15:177–183 (1985).

Kinsley et al., "St. Jude Medical Valve Replacement," *J. Thorac. Cardiovasc. Surg.* 92:349–360 (1986).

Lillehei, "Hemolysis and the St. Jude Medical® Valve," two-page technical data sheet published by St. Jude Medical, Inc. (Apr. 1987).

Morishita et al., "Fatal Hemolysis Due to Unidentified Causes Following Mitral Valve Replacement with Bileaflet Tilting Disc Valve Prosthesis," *Heart Vessels* 3:100–103 (1987).

Skoularigis et al., "Frequency and Severity of Intravascular Hemolysis After Left–Sided Cardiac Valve Replacement with Medtronic Hall and St. Jude Medical Prostheses, and Influence of Prosthetic Type, Position, Size and Number," *Am. J. Cardiol.* 71:587–590 (1993).

Taggart et al., "Severe Haemolysis with the St. Jude Medical Prosthesis," *Eur. J. Cardio-thorac. Surg.* 2:137–142 (1988).

WYKO Corporation eight-page brochure, circa Jan. 1992.

Tsuruta et al., "Accurate Measurement of Lens Thickness by Using White–Light Fringes", Japanese Journal of Applied Physics, 14, suppl. 14–1, pp. 369–372, 1975.

Geiger et al., "Non-destructive Evaluation of Prosthetic Heart Valves by Holographic Interferometry", J. Heart Valve Dis. 2, 3, May 1993, 343–347.

Zarubin et al., "Non-destructive Evaluation Techniques for Prosthetic Heart Valves Based on Hologram Interferometry, Part I", J. Heart Valve Dis. 2, 4, Jul. 1993, 440–447.

*Primary Examiner*—David H. Willse
*Attorney, Agent, or Firm*—Klarquist, Sparkman, Campbell, Leigh & Whinston

[57] ABSTRACT

A method for making bileaflet heart valve prostheses wherein leaflets with unacceptably rough leading edges are identified during production. The leaflet leading edge surfaces are subjected to optical surface profilometry so that leaflets with undesirable rough leading edge surfaces may be identified and eliminated from production or reprocessed. The leaflet leading edge is also provided with a domed contour that allows the surface of the bevel to be polished adequately.

11 Claims, 4 Drawing Sheets

Rt: 10.413 μm
MAG: 10.0

R2 LEAFLET, CENTER

FIG. 8

Rt: 10.542 μm
MAG: 10.0

V2 LEAFLET, CENTER

CENTER OF LEAFLET R2

CENTER OF VALVE V1

METHOD FOR MAKING AN ARTIFICIAL HEART VALVE

FIELD OF THE INVENTION

The present invention relates to artificial heart valves and more particularly to a method for ensuring the smoothness of leading edge surfaces on leaflets utilized in heart valves.

BACKGROUND OF THE INVENTION

Heart valve prostheses are well-known in the art as replacement mechanical valve devices for damaged or diseased natural heart valves. Bileaflet valves are a familiar example of an artificial heart valve to those skilled in the art. Among bileaflet valves, the St. Jude Medical Valve ("SJMV") or Prosthesis is well-known, having served as a replacement for hundreds of thousands of aortic and mitral heart valves since its introduction in 1977.

The SJMV is a popular choice for cardiac valve replacement because of its low-profile design and good hemodynamics. Statistically, the St. Jude valve has shown excellent performance in recipients of the valve. However, implantation of the SJMV may yield more sub-clinical hemolysis (disruption of red blood cells) in valve recipients than other comparable prostheses. Moreover, in a number of unexplained cases, SJMV recipients have developed serious hemolysis requiring reoperation, explantation, and replacement of the valve.

Sub-clinical hemolysis is common following the implantation of most types of artificial heart valves. The hemolysis has usually been attributed to mechanical shearing forces on erythrocytes (red blood cells) in the turbulent flow which may develop within the artificial heart valve prosthesis. The turbulence arises as blood moves through the zone of pressure gradient across the valve prosthesis. Leakage alongside the valve (paravalvular leakage) due to imperfect sutures or dehiscence (becoming loose) is also known to cause undesirable turbulence and hemolysis owing to the "jet effect." The shear forces act mechanically to damage the red blood cells, causing breakage which releases free hemoglobin and the enzyme lactic dehydrogenase (LDH) into the blood. This loss of red blood cells makes the marrow "push" immature erythrocytes ("reticulocytes") into the circulation.

Subclinical hemolysis is usually compensated for by increased bone marrow red blood cell production. Drug treatment such as iron therapy can also help. On the other hand, hemolysis may become life-threatening when severe anemia develops. Anemia, in turn, may both worsen the hemolysis and create iron-deficient red blood cells which are more vulnerable to damage. If not treated, significant hemolysis may lead to heart and renal (kidney) failure and eventually death. The treatment for severe hemolysis in SJMV recipients usually includes the hazardous reoperation and replacement of the hemolytic SJM valve.

Therefore, the cases of severe hemolysis accompanying SJMV replacement, while few in number, are a serious concern. Various studies have attempted to find the cause of this inexplicable severe hemolysis. While the studies have proffered a variety of explanations for some of the instances of hemolysis, other instances have gone unexplained. For instance, Kingsley et al. in "St. Jude Medical Valve Replacement" *J. Thorac. Cardiovasc. Surg.* 1986; 92:349-360, reports one SJMV recipient developing acute anemia necessitating blood transfusions. The patient had marked hemoglobinuria and renal failure. All other causes of hemolysis were excluded before re-operation and replacement of the SJMV with a xenograft (animal tissue) ten days after the first operation. No further hemolysis occurred. The explanted SJMV was analyzed at St. Jude Medical Laboratories and found to be structurally normal.

Five more cases of unexplained severe hemolysis in recipients of the SJMV are revealed by Taggart et al., in "Severe Haemolysis with the St. Jude Medical Prosthesis," *Eur. J. Cardio-thorac. Surg.* 1988; 2:137-142. No paravalvular leakage was found by echocardiography, or seen at re-operation, or at autopsy examination in those who died before reoperation could be effected. The explanted valves functioned satisfactorily in laboratory hemodynamic testing. Hemolytic anemia without paravalvular leakage was also reported in three SJMV recipients by Burckhardt et al., in "Heart Valve Replacement with St. Jude Medical Valve Prosthesis," *Valvular Heart Disease* Sept. 1988; 78:118-124.

The hemolysis accompanying the St. Jude valve has also been attributed to asynchronous closure of the valve leaflets causing excessive turbulence (Ferrière, "Hemolysis in Patients with Valve Prostheses, Comparison Between Bjork-Shiley and St. Jude Medical Prostheses," *Arch. Mal. Coeur* 1985; 78:1243.

Furthermore, scanning electron microscopy (SEM) has been utilized to study the flat surfaces of two St. Jude valves explanted from recipients who developed severe hemolysis. Both patients died (Morishita et al., "Fatal Hemolysis Due to Unidentified Causes Following Mitral Valve Replacement with Bi-Leaflet Tilting Disk Valve Prosthesis," *Heart Vessels* 1987; 3:100-103). The SEM identified a smooth elevated irregularity on the flat valve leaflet surface suspected of causing the severe hemolysis.

While SEM is desirable for studying aspects of heart valve prosthesis leaflets, its usefulness is circumscribed. For instance, SEM normally requires an irreversible deposition of gold or osmium upon an object to be studied. Thus, the use of SEM to screen SJMVs before implantation is impractical. Moreover, SEM analysis, even with the deposition of gold, may not provide information on some potentially important features of SJMVs, such as surface profile characteristics.

Despite various attempts to discover the causes of hemolysis in recipients of bileaflet heart valves, instances of serious hemolysis have gone unexplained in spite of rigorous study.

It is an object of this invention to provide an improved method of making heart valve prostheses to ensure uniform quality control of heart valve components.

It is a further object of this invention to provide for an improved method of making heart valve prostheses to identify heart valve prostheses that may cause hemolysis and to exclude or modify them to conform to a predetermined standard.

A final object of this invention is to understand the source of hemolysis in bileaflet tilting heart valve prostheses, and use that understanding in future valve design to reduce hemolysis in patients in whom those valves may be implanted.

These and other objects of the invention will be understood more clearly by reference to the following detailed description and drawings.

SUMMARY OF THE INVENTION

My invention is applicable to a bileaflet-type heart valve prosthesis serving as a replacement for either the mitral or aortic valves of the heart. In particular, the method of my invention is applicable to the manufacturing process of such a heart valve. Typically, the bileaflet valve has a pair of semi-circular leaflets with straight leading edges. The leaflets pivot within an opening in an annular frame to control the one-way flow of blood through the valve. When the leaflets pivot to the open position to allow a flow of blood through the valve, both of the leaflets present the straight leading edge of the semi-circle to the flow of blood. The leaflets have flat side surfaces trailing parallel to the direction of blood flow. The flat sides are bounded by the rounded trailing edges of the semi-circle.

When retrograde flow of blood through the valve is to be restricted, the leaflets pivot to close the frame opening. In the closed position, the leading edges oppose each other, separated by a narrow gap which bisects the frame opening. The rounded trailing edges of the leaflets impinge upon the inner surface of the annular frame. When the bileaflet valve is in the closed position, some reverse blood flow occurs through the region of the pivots and also through the narrow gap.

I have found that hemolysis may result in a patient with an implanted bileaflet artificial valve when the leaflet leading edge surfaces are rough and lack convexity along the lengths thereof. Because the flow of blood directly impinges upon the leaflet leading edges, the rough leading edge surfaces tend to tear and rupture erythrocytes. This mechanism of damage may occur most notably in the aortic position. Erythrocyte damage may also occur when the reverse flow forces red blood cells between the leading edges of the closed leaflets, especially in mitral valves. Therefore, the presence of a gap between the flat, rough leading edge surfaces, which allow some regurgitation (back flow) of blood, is also important. Damage may also occur when the erythrocytes are crushed between the leaflet leading edges when the leaflets close.

In spite of extensive prior research, the source of hemolysis in the leading edge has not previously been detected or appreciated because the roughness can only be appreciated on a microscopic level, using certain instruments. Moreover, previous techniques of microscopic examination (such as scanning electron microscopy (SEM)) have not detected the irregularity in the profile of the leading edge or similar irregularity on the flat side surfaces. SEM is not practical for examining the leaflet leading edges because the leaflet must be irreversibly coated with gold, effectively destroying the leaflet for purposes of further clinical use. Without the gold coating, the carbon surface of the leaflet absorbs, rather than reflects, the electrons emitted by SEM, yielding a featureless SEM image of the leaflet surface. Moreover, SEM methods do not adequately quantify some important surface features, such as surface roughness or surface convexity.

I have discovered that the leaflet leading edges have varying degrees of roughness, and that low degrees of roughness are unlikely to cause hemolysis, while higher degrees of roughness of the leading edge surface are more likely to cause hemolysis. The reverse is true of uniform convexity of the leading edge surface. Given the importance of relative degrees of roughness and convexity in causing hemolysis, it is impracticable to rely on the "look" of an image produced by SEM of a leaflet leading edge when screening the leaflets.

I have also discovered that the aforementioned problems may be obviated if the leaflets are made by the method of my invention. A preferred mode of my method for making a leaflet for a heart valve comprises the steps of: forming a leaflet having a straight leading edge that faces an upstream flow of blood when the heart valve is open; scanning the straight leading edge to determine the roughness of the edge; and selecting the leaflet for inclusion in a heart valve only if the roughness of the leading edge is less than a predetermined roughness value beyond which clinically unacceptable hemolysis tends to occur.

The method of my invention may also include the step of scanning the straight leading edge to determine the convexity of the leading edge surface. Only those valves with sufficient leading edge surface convexity are incorporated into the heart valve. The leading edge convexity scanning step may precede the leading edge roughness scanning step, or it may follow it.

When assembled, the valve leaflets should not have an appreciable gap between them in order to obviate any turbulent regurgitant jets at the micro level.

The present invention also includes products produced by any of the methods described herein.

DETAILED DESCRIPTION OF A PREFERRED EMBODIMENT OF THE INVENTION

The present invention includes a method of screening the roughness of the leading edges of leaflets of a bileaflet heart valve prosthesis, and the product produced by that method. In a preferred embodiment depicted generally in FIG. 1, the heart valve is a bileaflet heart valve prosthesis 10 for replacement of a heart mitral or aortic valve. Such a valve can be purchased from St. Jude Medical, Inc., of St. Paul, Minn., and is widely known in the field as the St. Jude Artificial Heart Valve. The bileaflet heart valve prosthesis 10 has an annular frame 12 with an opening 16 within which two leaflets 14 are pivotally held.

Figures 1, 2, 3, 4:
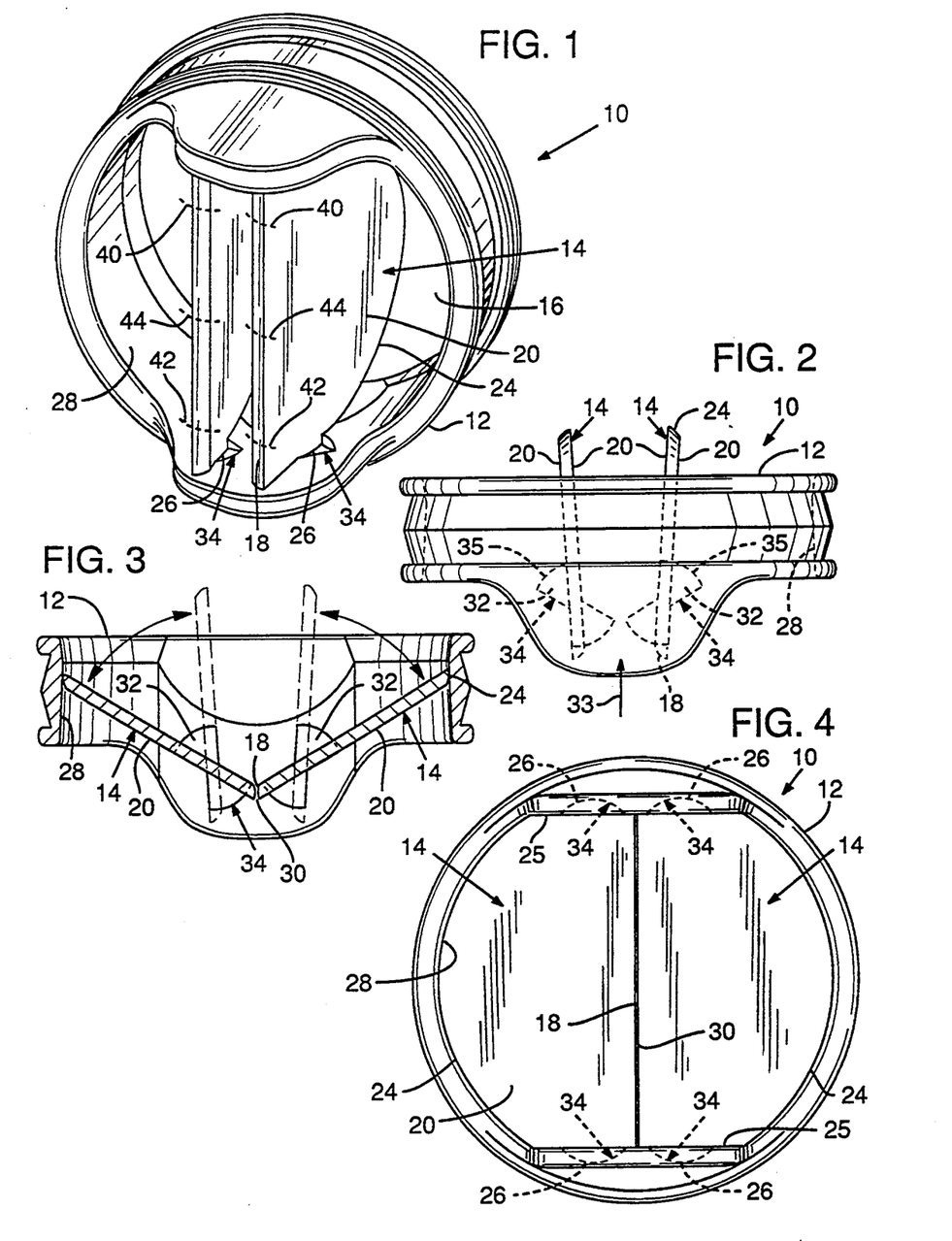
FIG. 1 is a perspective, inlet view of a bileaflet heart valve prosthesis of the present invention, with the bileaflet valve in an open position.
FIG. 2 is a side of a heart valve prosthesis of FIG. 1 in an open position.
FIG. 3 is a side view of a heart valve prosthesis of the present invention with the leaflets of the valve in a closed position, and the open position of the leaflets shown in phantom.
FIG. 4 is a top plan of a heart valve prosthesis of the present invention in a closed position.

The leaflets 14 pivot between an open and closed position to regulate the flow of blood through the mitral or aortic valve positions of the heart. The leaflets 14 are semi-circular with a straight leading edge 18 which faces the flow of blood when the prosthesis 10 is in the open position. Mitral valve leaflets may have a thickness of 360 to 400 microns. Flat side surfaces 20 extend from the leading edge 18 and are bounded by an arcuate trailing edge 24. The leading edges 18 are bevelled at about 60°-65° with respect to the side surfaces 20. Each leaflet 14 has two ears 26 (see FIG. 4) serving as pivot surfaces for the leaflets 14. The ears 26 are small arcuate protrusions that extend from side edges 25 that extend between either side of the leaflet straight leading edge 18 and the arcuate trailing edge 24. The ears 26 are received within butterfly-shaped recesses 34 in upper and lower portions of the interior surface 28 of the annular frame 12. Each wing 32 of the butterfly-shaped recesses 34 is cut in an angle within which the ears 26, and accordingly, the leaflets 14 are free to pivot. The butterfly-shaped recesses 34 have arcuate bottom surfaces 35 corresponding to the arcuate protrusions of the ears 26.

The leaflets of the valve open when upstream pressure on the valve exceeds downstream pressure. The valve would open, for example, during left atrial contraction or ventricular relaxation (for a mitral valve) or during ventricular contraction (for an aortic valve). In the open position, as shown in FIG. 2, the leaflets 14 are pivoted to a position wherein the leaflets 14 are almost parallel with one another, and with the flow of upstream blood 33 through the frame 12. In the open position, the leaflet leading edges 18 are directed at the direction of the flow of blood.

The leaflets of the valve pivot from the open position shown in FIG. 2 to the closed position in FIG. 3 when downstream pressure sufficiently exceeds upstream pressure, for example, during relaxation of the upstream chamber of the heart. In the closed position, as shown in FIG. 3, the leaflets 14 close the opening 16. The trailing edges 24 of the leaflets pivot to contact the inner surface of the annular frame 12. The bevelled leading edge surfaces 18 are pivoted toward each other to be positioned generally parallel with one another across a narrow gap 30. This linear gap between the opposing bevelled leading edges 18 bisects the opening 16. The leaflets in the closed position are each angled about 25°-30° from a plane radially across the annular frame 12. In this position, the leaflets 14 substantially occlude the valve orifice reverse blood flow through the valve. However, some regurgitant (reverse) flow occurs, which is discussed below.

In an exemplary embodiment, the heart valve prosthesis 10 is situated in the mitral position between the left atrium and left ventricle or between the left ventricle and the aorta of a human heart. The flow of blood 33 passes through the annular frame 12 from the left atrium to the left ventricle or from the left ventricle to the aorta. The heart valve prosthesis 10 is secured to the heart tissue with a plurality of sutures, usually between 15 and 25, depending on the technique used.

The heart valve prosthesis 10 functions when an increase in blood pressure in the left atrium moves the leaflets 14 to the open position as shown in FIG. 2. With the leaflets 14 positioned almost parallel to the flow of blood through the opening 16, the blood has an unobstructed flow through three passages within the opening 16: one passage between the leaflets 14, and two passages between the leaflets 14 and the inner surface 28 of the annular frame 12.

Damage to the red blood cells may occur in the open position when the leaflet leading edges 18 are rough. Because the leading edges are positioned directly across the flow of blood, red blood cells continuously contact and slide across the leading edges 18. Microscopic roughness in the leading edge surfaces tends to abrade these red blood cells, eventually disrupting many of the cells to release free hemoglobin and the enzyme lactic dehydrogenase, thereby contributing to hemolysis.

On increase of blood pressure in the left ventricle by its contraction, the flow of blood is reversed across the mitral heart valve prosthesis 10. The reversed flow of blood quickly pushes the leaflets 14 into the closed position shown in FIG. 3. In the closed position, reverse flow occurs around the trailing edges 24, particularly around the junction of the ears 26 within the butterfly recesses 34 (see FIG. 4), washing the region. A small amount of blood will also flow through the gap 30 between the leaflets 18 (see FIG. 5). This reverse flow after the valve closes is called "closed regurgitation."

Damage to the red blood cells may also occur in the closed position when be leaflet leading edges 18 are rough. Because the reverse blood flow is forced through the gap 30 (typically of a width approximating 6-7 diameters of a red blood cell), red blood cells are forced against the leaflet beveled leading edges 18 (see FIG. 3). Abrasion and breakage of the red blood cells may also occur if the leading edges are microscopically rough or by the rough leading edges catching and crushing red blood cells between them each time the leaflets close.

It should be understood that the microscopic roughness features herein described may be extremely small. Red blood cell damage may result when they slide over irregularities with dimensions of only a few dozen nanometers. The damaging roughness features, however, may be of other sizes as well.

Furthermore, while this description focuses on red blood cell damage due to rough leaflet leading edges 18, it should be understood that any prosthetic surface which is exposed to blood may damage the red blood cells if rough. For instance, the areas around the ears 26 and the butterfly recesses 34 may contribute to hemolysis if rough. The method described herein for identifying such rough surfaces may be applied effectively to any surface of the prosthesis.

The method of this invention helps avoid the development of clinical hemolysis in recipients of bileaflet heart valves, and especially recipients of the SJMV. Clinical hemolysis resulting from damage to the red blood cells may be indicated in a variety of ways. One important indication is dropping hemoglobin levels. In males and females, normal hemoglobin levels are around 12 to 17, and 11 to 16 grams of hemoglobin/deciliter (dl) of blood, respectively. Clinical hemolysis may be indicated when hemoglobin levels persist below the normal levels. Low hematocrit levels are also indicative of clinical hemolysis. The hematocrit level is the volume of red blood cells in a unit of blood expressed either as a percentage or as a ratio. Normal hematocrit levels are around 35 to 45%, and persistently lower hematocrit levels are indicative of anemia and possibly clinical hemolysis.

In a preferred method of the present invention, the leading edge surfaces 18 of the leaflets 14 are subjected to first and second scanning steps during production before the heart valve leaflets 14 are approved for implantation. The scanning steps are undertaken with an optical profilometer. The first scanning step ensures that the leading edges 18 have a surface convexity greater than a predetermined level. The second scanning step ensures that the leading edges 18 have a roughness below a predetermined roughness.

A preferred method for manufacturing the leaflets 14 provides for the deposition of pyrolytic carbon upon a leaflet substrate of graphite carbon. It is preferred that the substrate leading edge 18 surface have a profile that is slightly domed (convex) as at 38 along the length thereof (see FIG. 5), somewhat like the leading edge of an aeroplane wing. The domed profile contributes to the uniform, smooth deposition of the pyrolytic carbon coating and subsequent uniform polishing. It should be noted that the domed profile of the leading edge is so slight as to probably prevent visual appreciation with the naked eye. Thus, the domed profiles evident in FIGS. 1-3, and 5 are exaggerated to promote visual understanding of the domed shape.

The first scanning step with the optical profilometer occurs after the pyrolytic carbon coating is deposited upon the leaflet substrate, but before polishing. The leading edge surface 18 is measured to assure adequate surface convexity (domed profile) along the length of the leading edge 18. Only those leaflets with leading edges with convexities greater than a predetermined level are selected for polishing. Those leaflets with leading edges found to have less than the predetermined surface convexity are discarded or reprocessed. The reprocessing may constitute a reprofiling operation to obtain sufficient leading edge convexity. Such reprocessed leaflets may then be polished. Once polishing is complete, the leading edges are subjected to a second scanning step to determine the roughness of the polished leading edge. Leaflets are incorporated into the heart valve prosthesis 10 only if the roughness of the leading edges is less than a predetermined roughness beyond which clinically unacceptable hemolysis may occur, depending also upon the gap between the leaflets in the closed position. Leaflets with leading edges that are excessively rough may be discarded or reprocessed by repolishing.

A preferred device and method for determining the convex curvature and the roughness of the leaflet leading edge surfaces 18 is disclosed in U.S. Pat. No. 5,133,601 to Cohen et al., which is incorporated by reference herein. The device and method disclosed in Cohen et al. measures the curvature and the roughness of the leaflet leading edge surface 18 through the use of an interferometric profiler. The Cohen et al. device performs white light fringe pattern interferometry (FPI) using a modified Mirau interference microscope. Interferometric and digital signal processing algorithms produce accurate three-dimensional surface profile measurements, so that leaflets with undesirably flat or rough leading edge surfaces may be identified and eliminated from production or reprocessed.

Figure 6:
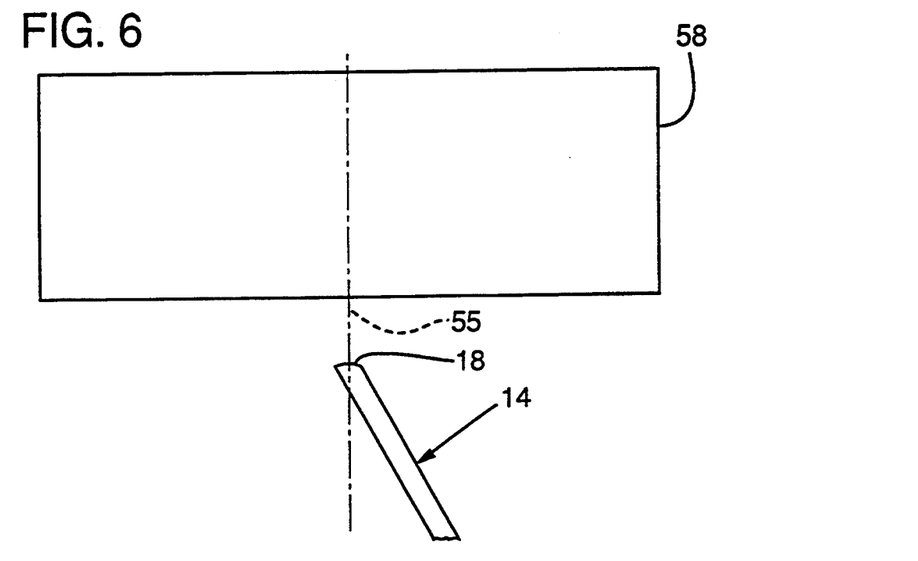
FIG. 6 is a schematic of the interferometric profiler used to measure the curvature and roughness of the leaflet leading edge surfaces of the heart valve prosthesis of the present invention. The leaflet is shown in a cross-sectional cut-away view.

FIG. 6 shows a schematic of an interferometric profiler 58 generally according to that disclosed in Cohen et al. A leaflet 14 is positioned within a vise (not shown) upon the stage (not shown) of the profiler 58. The leaflet 14 is held so that the surface of the beveled leaflet leading edge 18 is held perpendicular to a vertical axis 55 of the profiler 58. So held, the leaflet leading edge 18 may be scanned. The operation of the profiler is explained in detail in Cohen et al. The Cohen et al. profiler operates rapidly enough so that the convexity and roughness measurement steps may be integrated as a part of the heart valve prosthesis 10 manufacturing process.

Commercially, the Cohen et al. method may be implemented by utilizing a WYKO Corporation Rough Surface Tester Model RST. The Model RST is a vertically scanning interference microscope with magnification objectives of 2.5×, 10×, 20×, and 40×. The Model RST analyses provide average roughness ($R_a$), root mean square or rms roughness ($R_q$), and maximum peak-to-valley distance ($R_t$), which values are useful in assessing the permissible surface roughness and convexity of leaflet leading edges 18.

Figure 11:
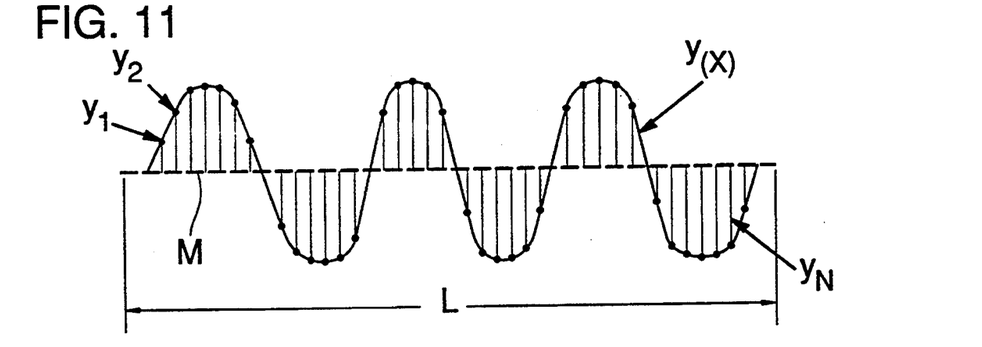
FIG. 11 is a graphic illustration aiding in the description of the surface parameters $R_a$ and $R_q$.

$R_a$ and $R_q$ can be better understood by referring to FIG. 11. Given a surface profile with length L represented by the function y(x) or by a set of digitized points $Y_1, Y_2, \ldots Y_n$, $R_a$ is the average deviation of that profile from the mean line (M). Geometrically, it is given by the total shaded area divided by the distance L; analytically, it is given by the integral over O to L of the absolute value of y(x), $R_a = 1/L \int_o^L |y(x)| dx$; and digitally, it is the sum of the various $y_i$'s divided by the total number of them, N, $$R_a = \frac{1}{N} \Sigma |y_i|.$$

The rms deviation of the profile from the mean line ($R_q$) is a similar parameter and is computed as $$R_q = \sqrt{\frac{1}{N} \Sigma y_i^2}\ .$$

Figure 5:
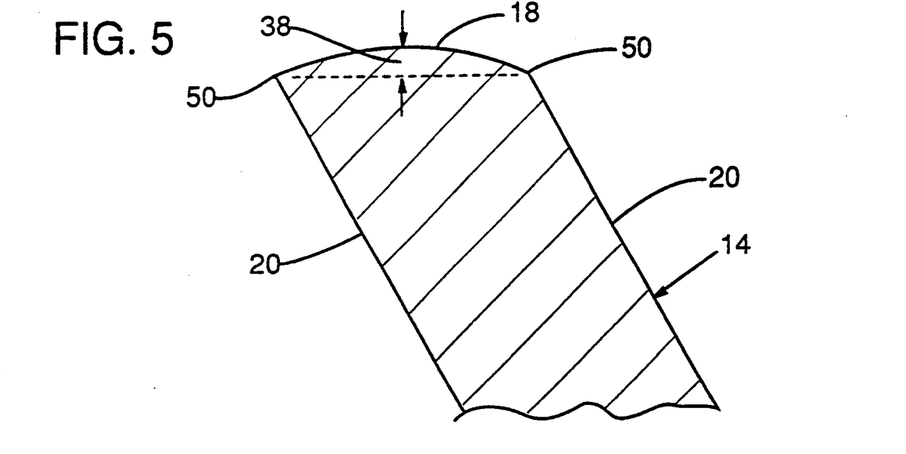
FIG. 5 is a cross-section to an enlarged scale of a leaflet leading edge surface of the heart valve of the present invention, showing a domed profile (the profile is accentuated for visual clarity).

$R_t$ represents the maximum peak-to-valley distance of a surface profile. As shown in FIG. 5, $R_t$ is the vertical dome height 38 between the highest point on the peak of the convex dome and the lowest point on the convex leading edge 18 profile. This lowest point will usually be the bottom of the domed leading edge at the intersections 50 with the flat side surfaces 20. However, grooves or other voids may penetrate below the level of the intersection 50, in which case the $R_t$ would be measured from the vertically lower groove bottom.

In a preferred method (further explained in the example below), the Model RST scans the leading edge 18 at a magnification of 10× in the first scanning step to determine the peak-to-valley distance value of the surface of the leaflet leading edge 18. The Model RST is set at a magnification 40× for the second scanning step to determine the values for the leading edge average roughness and rms roughness.

The convexity obtained in the first scanning step is a useful early indication of leaflet leading edges 18 that may cause hemolysis. In the example below, a scan determining a maximum peak-to-valley distance is made across each of three positions across the leaflet leading edge 18. In FIG. 1, these positions (left, right, and center) are denoted by dashed lines 40, 42, 44. The average value of these three maximum peak-to-valley distances is used to determine whether the leading edge 18 has acceptable convexity. As explained above, the deposition of pyrolytic carbon may be more uniform, and therefore less rough, when the leaflet leading edge has a convex dome 38 along its entire length. The domed cross-section also lends to smooth polishing of the leading edge 18. FIG. 5 shows the convex dome 38 on the leading edge 18 (wherein the dome height is accentuated to permit visual appreciation).

The convex dome height 38 may be optimal when the value for the average peak-to-valley distance is above a predetermined peak-to-valley value of about four microns. Alternatively, a desirable height for the convex dome is more than about one percent of the width of the beveled leading edge. The convex dome 38 measurement of the first scanning step is useful in identifying possibly deficient leaflet leading edges early in the manufacturing process (i.e., before polishing). If the leaflet leading edge profile has an inadequate average peak-to-valley distance, the leaflet simply may be discarded, or subjected to reprocessing. The reprocessing may be a reprofiling process on the leaflet leading edge 18 to obtain an acceptable average peak-to-valley distance for the cross-sectional profile of the leading edge 18.

The results of the second scanning step are especially important in determining when the leaflet leading edges 18 may cause hemolysis. It has been found that hemolysis may occur when the $R_q$ value of the surface of a leaflet leading edge 18 is above about 45 nanometers (nm). Leading edge 18 $R_a$ values that may cause clinically unacceptable hemolysis are those above about 35 nm. Those leaflets with leading edge roughness in excess of the foregoing $R_a$ and $R_q$ values may be discarded or subjected to reprocessing. Reprocessing in this case may be repolishing to obtain leading edges of acceptable roughness. As will be described in the forthcoming example, the $R_a$ and $R_q$ values of a preferred method may be the average values of a plurality of scans across a leaflet leading edge. In a preferred method, three scans are taken at the middle of the positions 40, 42, 44 (FIG. 1). Average values for $R_a$ and $R_q$ are calculated therefrom.

The specifics of the method of the present invention are further described in the following example. The example took place in an experimental setting, and leaflets from an explanted valve and a reference valve were analyzed.

EXAMPLE

An 80-year-old man presented in July 1991 with congestive heart failure due to mitral stenosis and coronary insufficiency. He underwent mitral valve replacement with a size 31 mm St. Jude mitral valve and two aortocoronary vein grafts. The mechanical valve was chosen because of his chronic atrial fibrillation, requiring anticoagulation. He was discharged two weeks after surgery with a hemoglobin of 9.2 g/dl. He was re-admitted three weeks later with tiredness, anorexia, dark urine and the same hemoglobin, but no melena. Echocardiography revealed a possible slight paravalvular leak. He was transfused on this and two other occasions, and was later re-admitted for exploration of his St. Jude mitral valve in October 1991. Prior to surgery, his hemoglobin was 9.3 g/dl, hematocrit 26.3%, reticulocyte count 4.1%, aspartate amino transferase 90 IU/l (reference range 18–44 IU/l), and lactic dehydrogenase 3004 IU/l. His urine was weakly positive for bilirubin.

At operation, there was a thin film of fibrin over the sewing ring (Coumadin had been stopped five days before), but the valve was in apparent good working order, and thorough examination failed to show a paravalvular leak. Search for the latter was especially diligent in view of the echo findings. The valve was replaced with a 30 mm ball-valve. The patient was discharged a week later with a hemoglobin of 12.2 g/dl. He has since maintained satisfactory hematological parameters with no evidence of clinical hemolysis during fourteen months of follow-up.

The explanted valve was inspected under up to 50× magnification with a conventional light microscope and was found to be structurally sound. Pulsatile flow testing, using a mixture of glycerine and saline, at a mean cardiac output (MCO) of 1.9 l/minute and heart rate of 70/min produced 17.5% regurgitation, which fell to 9.3% when the MCO rose to 5.1 l/min. This was 2% and 0.6%, respectively, less than the regurgitation from a standard test valve.

The beveled leading edge of each explanted leaflet was then subjected to the first and second scanning steps with a WYKO Corporation Rough Surface Tester Model RST optical profilometer at a magnification of 10× and 40×, respectively.

Figure 7:
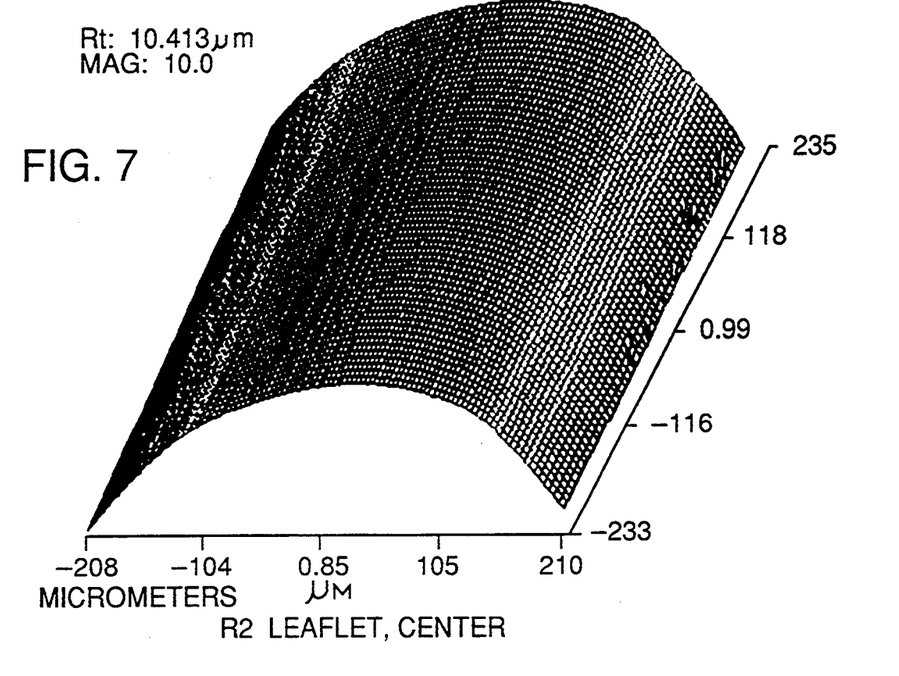
FIG. 7 is an interferometric profile taken at magnification 10× of the leading edge of a non-hemolytic bileaflet valve having a smooth, arcurate surface.
Figure 8:
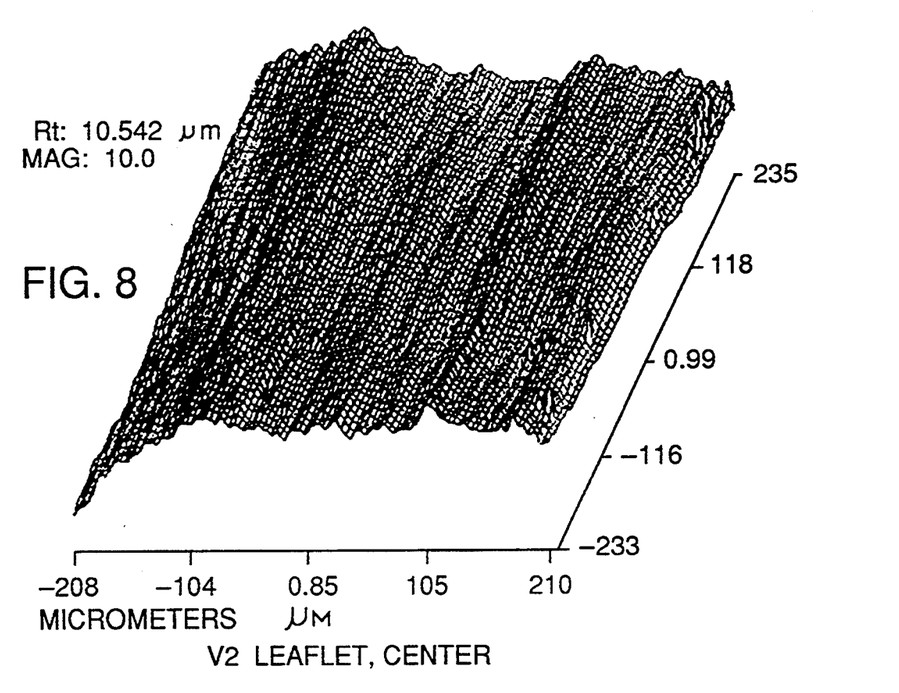
FIG. 8 is an interferometric profile taken at magnification 10× of a hemolytic valve showing irregularity of the leading edge surface of a hemolytic valve.

The cross-section of the leading edge of each explanted leaflet showed little curvature (FIG. 8) and was rather flat and irregular. Consistency was ascertained by scanning across the entire length of the leading edges before taking any readings. As shown in FIG. 1, the scans were recorded at three positions on each leaflet leading edge: right 42, left 40, and center 44. FIG. 8 shows a profile taken across the center 44 of the hemolytic leaflet leading edge. The three hemolytic leaflet scans were all similar in surface texture and topography. The leading edges of a reference St. Jude mitral valve that had not been implanted were similarly scanned. FIG. 7 shows the center position 44 scan of a reference valve leaflet. The reference valve leading edges had smoother texture and were gently domed. This difference in height of dome was shown by peak-to-valley ($R_t$) values between 6 and 11 microns in the reference valve as compared to less than 2 microns for the explanted hemolytic valve. The $R_t$ value included also the irregularity of the surface terrain. Under the method of the present invention, the explanted hemolytic valve leaflet with the flat leading edge profile would have been identified and discarded or reprocessed.

Figure 9:
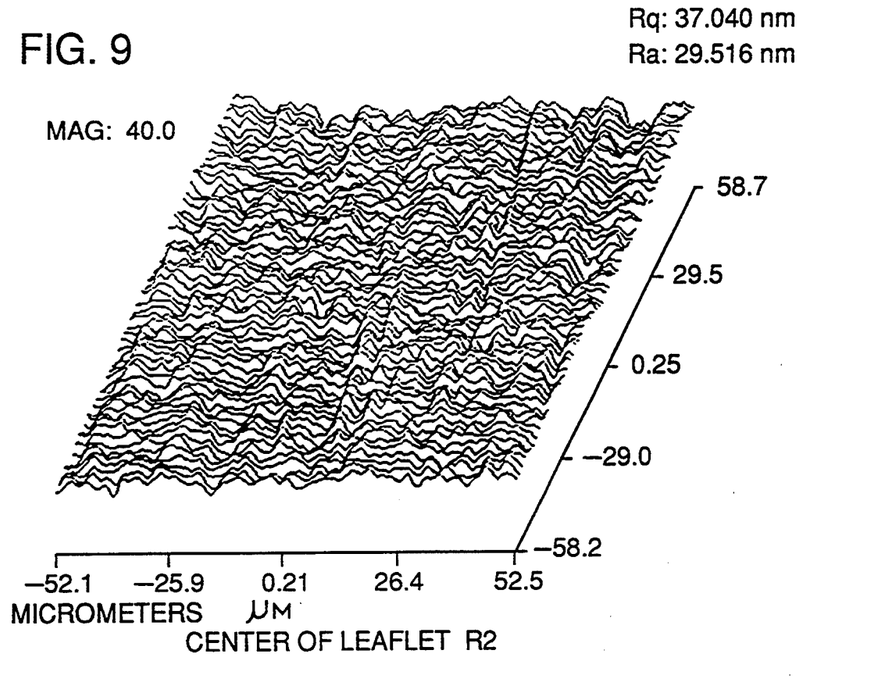
FIG. 9 is an interferometric roughness profile taken at magnification 40× of a center portion of the leading edge surface of a non-hemolytic valve, showing a roughness average $(R_a) = 29.5$ nm.
Figure 10:
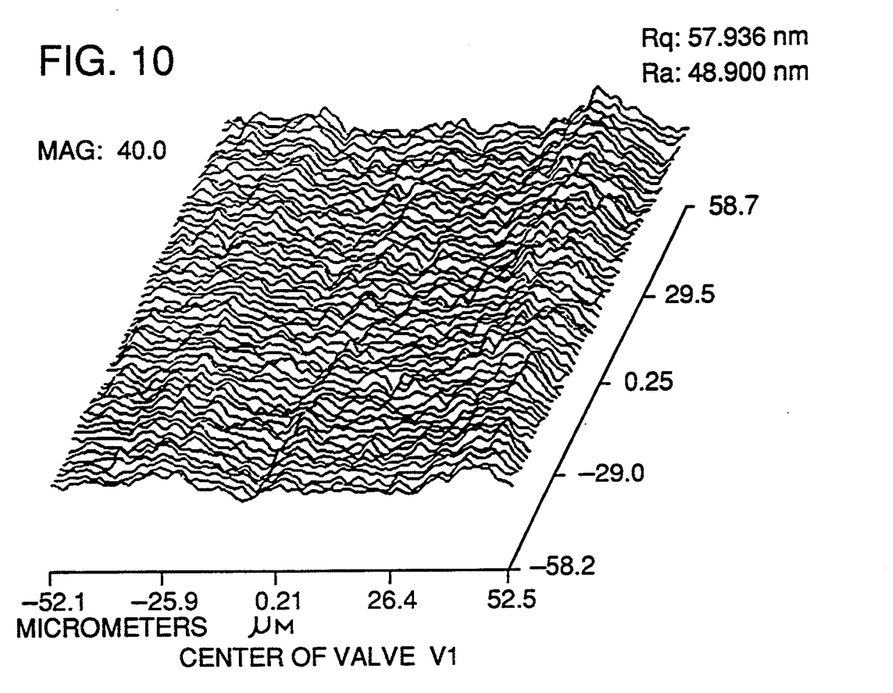
FIG. 10 is an interferometric roughness profile taken at magnification 40× of a center portion of the leading edge surface of a hemolytic valve, showing a roughness average $(R_a) = 48.9$ nm.

To better assess roughness, the second scanning step was taken under a magnification of 40× (FIGS. 9 and 10). The second set of scans focused on much smaller areas at the middle of the leading edge at scan positions 40, 42, and 44 and eliminated most of the curvature, allowing a truer-to-scale comparison of roughness to be made. As shown in Table 1, for each leaflet leading edge 18, three values of each of $R_a$ and $R_q$ were calculated. From these values, average values for $R_a$ and $R_q$ were computed by the WYKO Model RST. Judged in this way, the explanted hemolytic valve had about 40% more roughness than the reference valve. The leaflet flat side surfaces 20, which receive the push of systole, were also examined under magnification 40×. The roughness of the flat sides was comparable in both valves with similar $R_a$ values equal to 16–19 nm. Each leaflet leading edge 18 is 23 mm long and 420 microns wide, presenting a combined surface area of about 19.3 mm$^2$ to the flow of blood. Under the method of the present invention, the hemolytic valve leaflets with the excessively rough leading edges would have been identified and discarded or reprocessed.

The unusual flatness and roughness of the hemolytic valve were underscored by subsequent testing of eight more SJMVs. Three had been explanted for reasons other than hemolysis, and five had never been implanted. Although FPI showed varying flatness and roughness of the valve leaflets' leading edges, the hemolytic valve leaflet leading edges were by far the roughest and flattest along their entire length. In applying the method of this invention to the heart valve manufacturing process, valve leaflets with leading edges like those of the explanted hemolytic valve would be identified and discarded or reprocessed.

TABLE 1

Profile values of the leading edge of the leaflets of the reference and explanted hemolytic St. Jude valves

| Valve Type/Size | Leaflets | Corresponding Figures | Leading Edge Texture (nm) | |
|---|---|---|---|---|
| | | | $R_q$ | $R_a$ |
| Reference Mitral Valve | Leading Edge 1 | | 33,34,34 [34] | 26,27,27 [27] |
| | Leading Edge 2 | FIG. 9 | 47,37,45 [43] | 35,30,35 [33] |
| Hemolytic Mitral Valve | Leading Edge 1 | FIG. 10 | 44,58,58 [53] | 37,49,47 [44] |
| | Leading Edge 2 | | 49,75,81 [68] | 38,65,65 [56] |

The trios of values of $R_q$ and $R_a$ correspond to the left, center, and right scan results, respectively. Average values are in brackets directly below the trios of individual values. Bold values correspond to values in FIGS. 9 and 10.

While the value of the dome 38 height may be useful in determining whether a leaflet leading edge 18 may cause hemolysis, it is to be understood that it is probably only indirectly important in causing hemolysis: lack of dome tends to be associated with roughness, and a high dome probably lends itself to being better polished. A smooth leading edge, regardless of convex dome height, will help eliminate hemolysis. Therefore, it should be understood that the first screening step is of secondary importance. In face, a very flat leading edge probably may not cause hemolysis if it is very smooth. Accordingly, the first screening step may be eliminated without departing from the scope of the present invention.

It is also to be understood that many permutations of dome height and surface roughness may yield leaflet leading edges which do not cause hemolysis. For instance, as the elevation of the domed profile increase, the walls of the dome become steeper and may model the leading edge of an aeroplane wing with more linear flow, and thus less probability of hemolysis.

It is also to be understood that the number of scans across each leaflet leading edge can be varied from the three shown in the preferred method without departing from the scope of the invention. For instance, scans across six positions on the leading edge may be used to determine average $R_t$, $R_a$, and $R_q$ values.

While the interferometric profiler method disclosed in Cohen et al. is a preferred method of the present invention, it should be understood that other measurement techniques may work equally as well. For instance, "laser speckle" may be used to determine the roughness of the leaflet leading edge 18. When coherent (laser) light is reflected from a surface, laser speckle results when the light reflects off irregularities with dimensions greater than the wavelength of the coherent light. Using this method, a level of unacceptable leading edge roughness is chosen. Laser light with a wavelength equal to surface irregularities corresponding to that level of roughness is then reflected off the leaflet leading edge 18. Any irregularities whose scale is greater than the wavelength of the laser light will cause laser speckle. If film or other devices are available to observe light of this wavelength, leading edge surface roughness may be screened in this way.

It is to be understood that all methods for determining the surface roughness of the leaflet leading edge 18 fall within the scope of the present invention. For instance, conventional visible light microscopy may be used if the roughness to be detected has a relatively great scale. Moreover, it is to be understood that the method of the present invention may be applied to any surface of the heart valve prosthesis 10 which is exposed to the flow of blood.

While the foregoing detailed description has applied to the SJMV, it should be understood that the present invention may be applied equally as well to all bileaflet heart valves, including those made by CarboMedics, Inc., Austin, Tex., Baxter Health Care Corporation, Irvine, Calif. and Sorin Biomedical, Inc., Irvine, Calif. Furthermore, it should be understood that all configurations of heart valves may be made and improved upon under the present invention.

Having illustrated and described the principles of the invention in a preferred embodiment, it should be apparent to those skilled in the art that the invention can be modified in arrangement and detail without departing from such principles. I claim all modifications coming within the spirit and scope of the following claims.

I claim:

1. A method of making a leaflet for a heart valve for regulating a flow of blood, comprising the steps of:
   forming a leaflet having a straight leading edge that faces an upstream flow of blood when the valve is open; scanning the straight leading edge with an optical profile interferometer to determine if the convexity of the surface profile of the straight leading edge is above a predetermined value;
   if the convexity is above the predetermined value, then scanning the straight leading edge to determine the roughness of the straight leading edge; and
   incorporating the leaflet into the heart valve only if the roughness of the straight leading edge is less than a predetermined roughness value beyond which clinically unacceptable hemolysis tends to occur.

2. The method of claim 1, wherein said leaflet is incorporated into the heart valve only if the convex profile of the leading edge has a height more than about one percent of the width of the leading edge.

3. The method of claim 1, wherein the scanning of the leading edge with an optical profilometer comprises scanning by white light fringe pattern interferometry using a Mirau interference microscope system.

4. The method of claim 1, wherein the step of scanning the leading edge comprises scanning the leading edge over a plurality of positions.

5. The method of claim 1, wherein the roughness of the leading edge is calculated as a roughness average, and the predetermined roughness value is a roughness average of 35 nanometers.

6. The method of claim 1, wherein the roughness of the leading edge is calculated as a root mean square roughness, and the predetermined roughness value is a root mean square roughness of 45 nanometers.

7. A method for making a heart valve prosthesis that regulates the flow of blood in the heart, comprising the steps of:
- forming a semi-circular leaflet having a thickness and a straight leading edge and an arcuate trailing edge;
- performing a first scanning step on a surface profile of the leaflet leading edge with an optical profile interferometer to determine the convexity thereof;
- polishing the leaflet leading edge when the convexity thereof is above a predetermined value below which clinically unacceptable hemolysis is prone to occur;
- reprocessing the leaflet when the convexity thereof is below the predetermined value, the reprocessing being a reprofiling process on the leaflet leading edge so that the convexity thereof is above the predetermined value, the leaflet leading edge thereafter being polished;
- performing a second scanning step on the leaflet leading edge with an optical profile interferometer to obtain a value for the leading edge average roughness and root mean square roughness;
- determining whether the roughness average of the leading edge is above a predetermined roughness average value above which clinically unacceptable hemolysis is prone to occur;
- determining whether the root mean square roughness of the leading edge is above a predetermined root mean square value above which clinically unacceptable hemolysis is prone to occur; and
- incorporating the leaflet into the heart valve prosthesis only if both the roughness average and the root mean square roughness are less than the predetermined roughness average value and predetermined root mean square value, respectively, with the leaflet incorporated into the valve so that the leading edge faces the upstream flow of blood when the valve is open, and opposes the leading edge of an adjacent leaflet in the heart valve when the heart valve is in a closed position.

8. The method of claim 7 wherein the predetermined convexity value is more than about four microns.

9. The method of claim 7 wherein the predetermined convexity value is more than about one percent of the width of the leaflet leading edge.

10. The method of claim 7 wherein the predetermined roughness average value is 35 nanometers.

11. The method of claim 7 wherein the predetermined root mean square value is 45 nanometers.

* * * * *